(12) United States Patent
DeCesare et al.

(10) Patent No.: US 8,066,704 B2
(45) Date of Patent: Nov. 29, 2011

(54) SUCTION ABLATOR

(75) Inventors: Michael DeCesare, New Port Richey, FL (US); Hugh S. West, Jr., Salt Lake City, UT (US)

(73) Assignee: Linvatec Corporation, Largo, FL (US)

( * ) Notice: Subject to any disclaimer, the term of this patent is extended or adjusted under 35 U.S.C. 154(b) by 771 days.

(21) Appl. No.: 12/213,556

(22) Filed: Jun. 20, 2008

(65) Prior Publication Data

US 2009/0318918 A1 Dec. 24, 2009

(51) Int. Cl.
*A61B 18/18* (2006.01)
(52) U.S. Cl. .......................................... 606/49; 606/41
(58) Field of Classification Search .............. 606/27–31, 606/41–42, 48–49; 604/21–35, 39, 118–120
See application file for complete search history.

(56) References Cited

U.S. PATENT DOCUMENTS

| | | | | |
|---|---|---|---|---|
| 6,010,476 A | * | 1/2000 | Saadat | 604/22 |
| 6,210,378 B1 | * | 4/2001 | Ouchi | 604/264 |
| 6,379,350 B1 | * | 4/2002 | Sharkey et al. | 606/41 |
| 6,757,565 B2 | | 6/2004 | Sharkey et al. | |
| 7,150,746 B2 | * | 12/2006 | DeCesare et al. | 606/41 |
| 7,244,256 B2 | | 7/2007 | De Cesare et al. | |
| 7,837,683 B2 | * | 11/2010 | Carmel et al. | 606/41 |
| 2007/0149965 A1 | * | 6/2007 | Gallo et al. | 606/41 |

* cited by examiner

*Primary Examiner* — Linda Dvorak
*Assistant Examiner* — Brian M Antiskay
(74) *Attorney, Agent, or Firm* — Michael De Angeli

(57) ABSTRACT

An improved electrode for electrosurgery comprises at least one orifice in the active surface of the electrode connected to a lumen in the probe of larger cross-sectional area than the area of the orifice(s), the lumen being connected to a vacuum, such that a venturi is formed extending from the one or more orifices in the active surface of the electrode to the lumen, whereby flow of fluid, ablated tissue, and other debris in the vicinity of the surgical site is accelerated through the orifice(s), reducing clogging, whereby any particle passing through the orifice(s) is unlikely to become clogged downstream, and whereby the edges of the orifice(s) are ablative, tending to reduce any particles caught at the orifice(s) to a size small enough to pass therethrough.

4 Claims, 9 Drawing Sheets

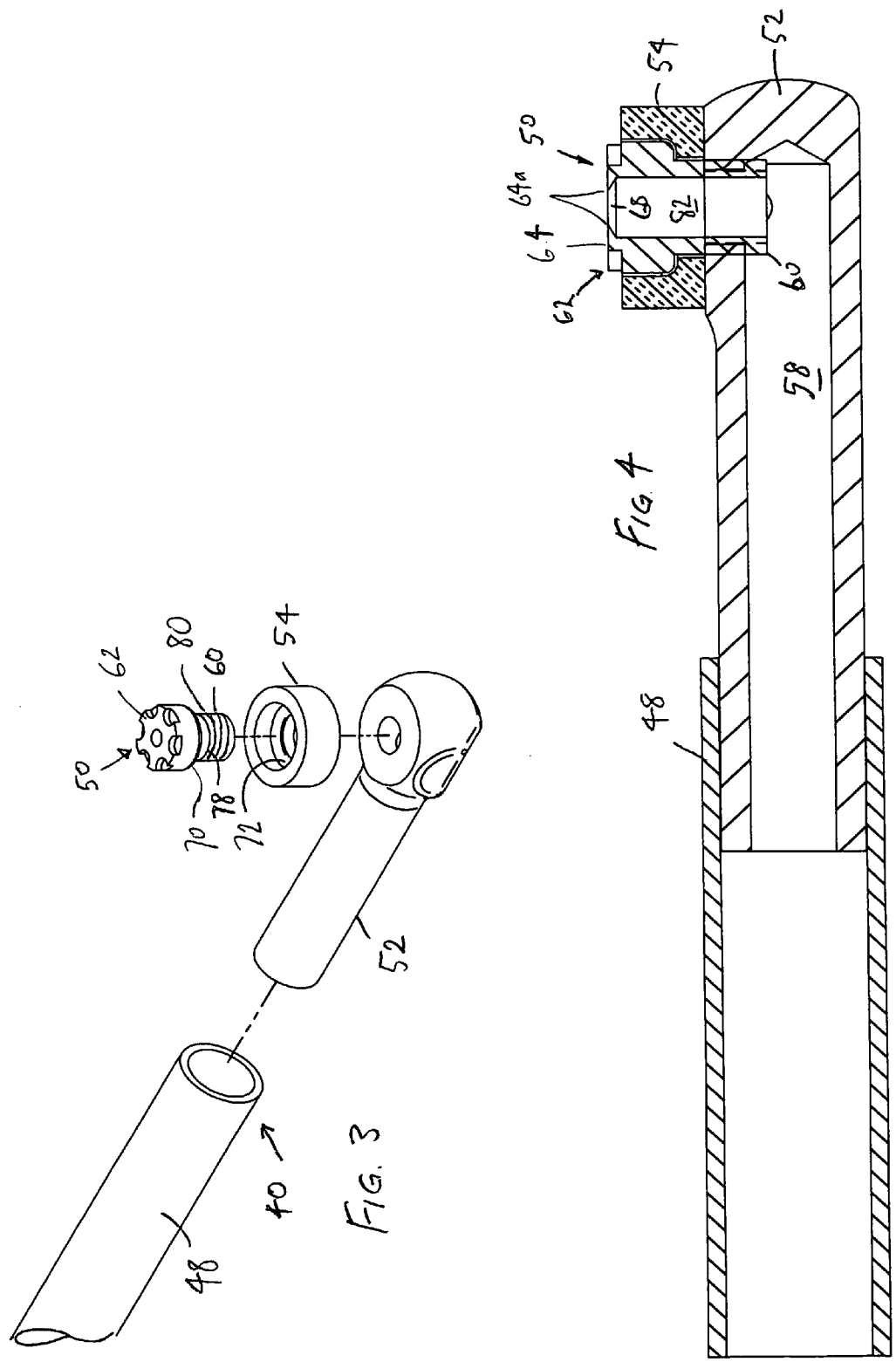

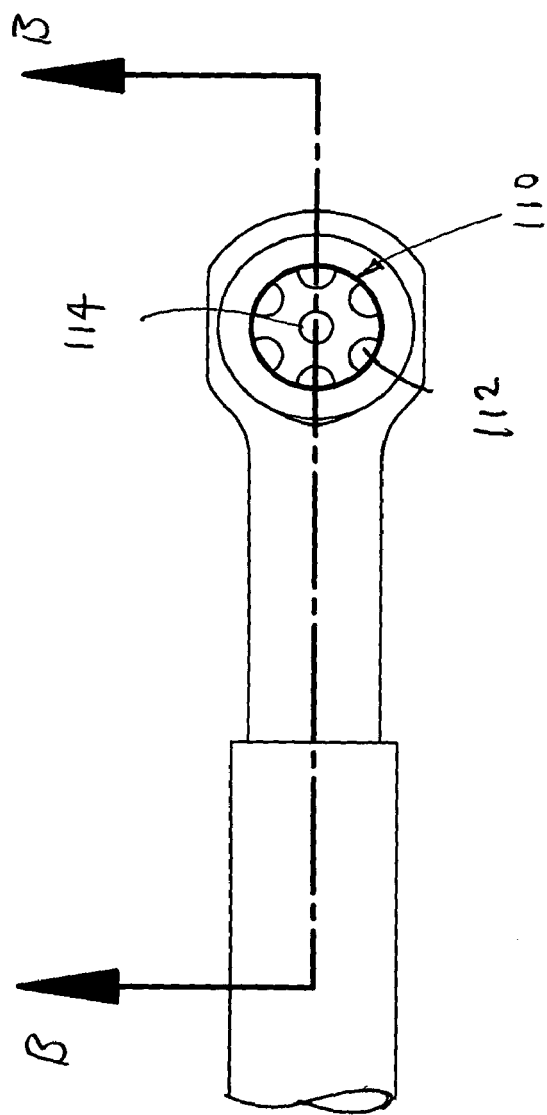
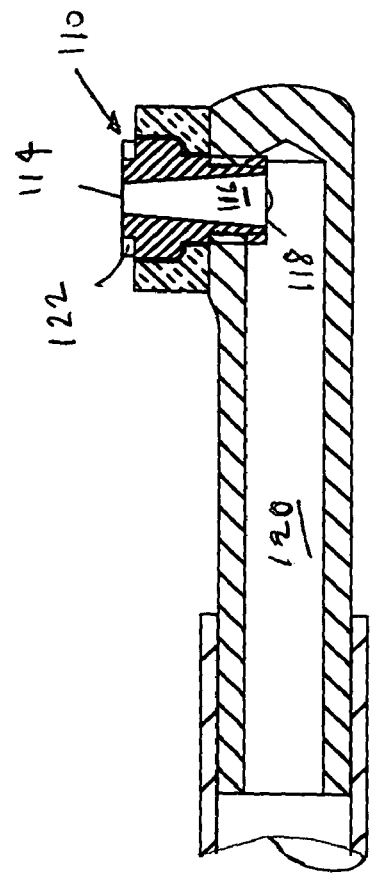
FIG. 8(a)
FIG. 8(b)

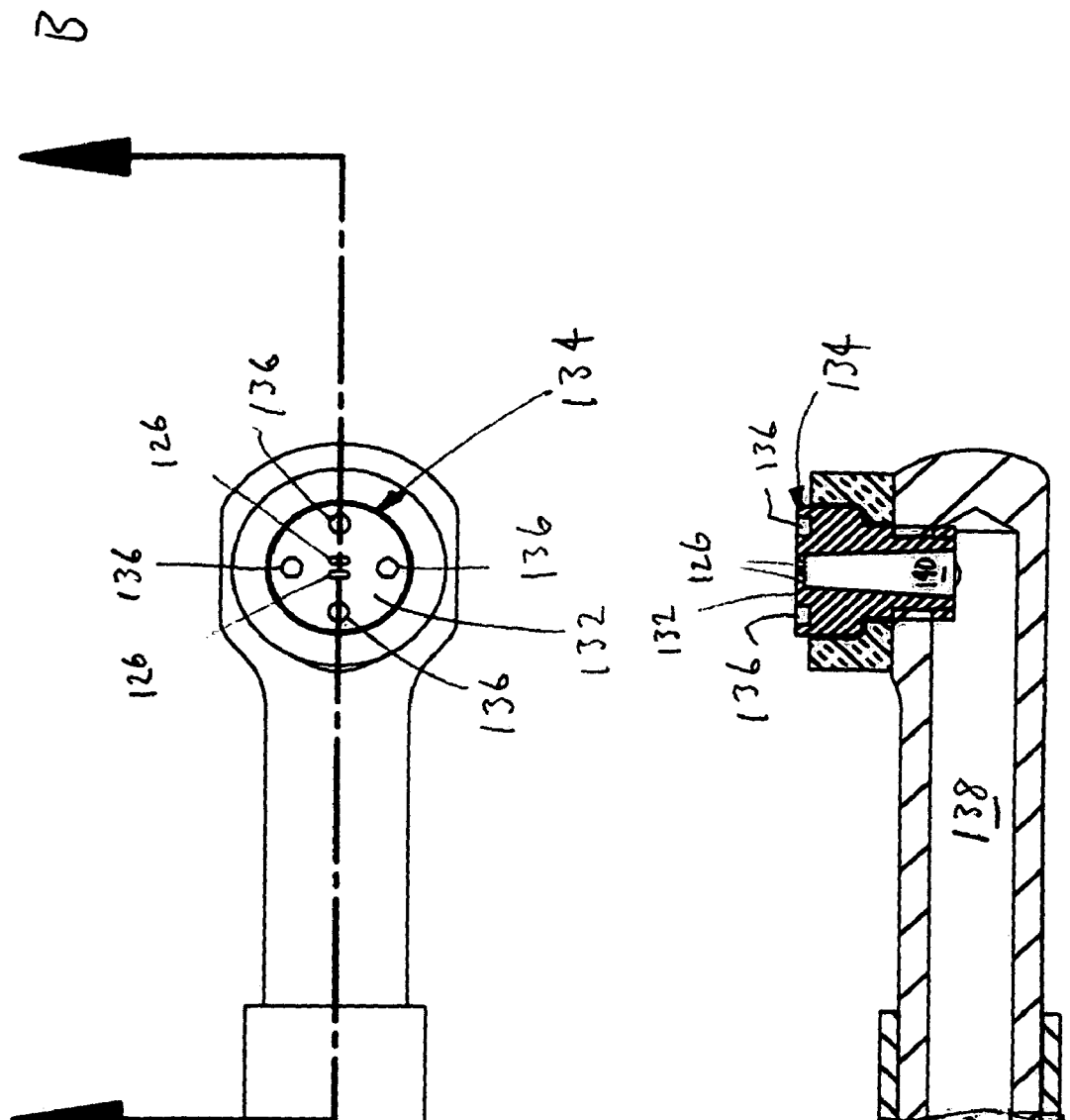

SUCTION ABLATOR

BACKGROUND OF THE INVENTION

1. Field of the Invention

The present invention relates to electrosurgical devices for ablating tissue in a surgical procedure. More specifically, the present invention relates to electrosurgical devices having an improved electrode design.

2. Relevant Technology

An arthroscope is an instrument used to look directly into a surgical site. Typically, the arthroscope utilizes a magnifying lens and coated glass fibers that beam an intense, cool light into the surgical site. A camera attached to the arthroscope allows the surgeon to view the surgical site on a monitor in the operating room. With the arthroscope, the surgeon can look directly into a surgical site, such as a knee or shoulder, to diagnose injury and decide on the best treatment. While viewing the surgical site with the arthroscope, the surgeon can repair an injury using a separate surgical instrument.

The ability to view the surgical site in this manner allows for a minimally invasive procedure. In recent years, arthroscopic surgeries have been developed for surgical procedures that traditionally were once very complicated and time consuming. Many of these surgeries are now performed as outpatient procedures using arthroscopic techniques.

At the beginning of the arthroscopic procedure, the patient receives an anesthetic. After the patient has been sufficiently anesthetized, the surgeon makes a plurality of incisions, known as portals, from the exterior of the body of the patient to the surgical site. Three portals are usually made: a first for the arthroscope, a second for the surgical instrument, and a third to permit fluids to escape from the surgical site. Sterile fluid, e.g., saline solution, is generally introduced by way of the arthroscope through the first portal. The sterile fluid serves among other purposes to expand the area of the surgical site. The introduction of sterile fluid makes it easier to see and work inside the body of the patient at the surgical site.

"Electrosurgical" instruments are commonly used in arthroscopy to ablate and/or coagulate tissue. In electrosurgery, a high-frequency current is applied to an electrode near or touching body tissue. As discussed in further detail below, at lower power levels the high-frequency current can be used to heat tissue through direct conduction, and at higher power levels can be used to form a plasma providing sufficient heat to ablate tissue. The present invention relates to improvements in such electrodes.

The electrosurgical electrode serves as one pole whereby a circuit is completed such that the high-frequency electrical current flows. In "monopolar" electrosurgery the return electrode is a patch placed elsewhere on the patient, so that the circuit is completed by energy being dissipated into the tissue and passing through the patch. In a "bipolar" electrosurgical device, the return electrode is placed in a separate location on the electrosurgical device. Energy leaving the electrode passes through fluids and/or tissue and returns to the return electrode on the electrosurgical device. The improved electrode of the present invention can be used in either monopolar or bipolar electrosurgery.

In both monopolar and bipolar electrosurgery, an electrode transfers energy to the surrounding fluid. The energy can be controlled to simply heat the adjacent tissue or to cut or ablate the tissue. Heating of the tissue is often done to facilitate coagulation, that is, to stop bleeding.

To ablate tissue, larger amounts of energy are applied to the electrode. The electrode generates enough heat to create gas bubbles around the electrode. The gas bubbles have a much higher resistance than tissue or saline solution, which causes the electrode voltage to increase. Given sufficient power the electrode discharges (i.e., an arc is formed). The high voltage current travels through the gas bubbles and creates a plasma discharge over the surface of the electrode. If the electrode is moved sufficiently close to tissue the plasma discharge is effective to ablate the tissue.

The contours and surface area of an electrode are important for controlling where arcing occurs on the electrode and how much power is required to cause a discharge. More specifically, arcing occures preferentially where current density is greatest in the electrode; in general, current density is maximized at sharp edges. Arcing, and thus the ability of the electrode to form an effective ablative tool, can be thus be encouraged by forming electrodes or electrode edges with small surface areas. Typically, sharp edges, that is, members of small surface areas where current density is concentrated, are created on the distal face of an electrode by forming grooves therein or assembling small-diameter wires to the body of the electrode so that the wires form edges of small surface area. See commonly-assigned U.S. Pat. Nos. 7,244,256 and 7,150,746 to the present inventors.

An important aspect of the design of an electrode for electrosurgery is that non-active surfaces must be electrically isolated from electrically conductive materials such as the saline solution on the exterior of the electrode, so that electrical conduction via these materials does not ground the circuit and prevent the electrode from delivering its current to the active surface. For example, wires or conducting materials that deliver current through the probe to the active surface need to be electrically isolated from the exterior of the probe, which can come into contact with body tissues during a procedure.

Much of the length of an electrosurgical probe is coated with an insulator or has lead wires that run inside insulated tubing. Near the active surface, however, insulating the electrodes becomes more difficult because of the extreme heat generated at the active surface. Many existing electrosurgical devices use an insulator such as a ceramic member to separate the active portion of the electrode from the remainder of the probe, both electrically and thermally. U.S. Pat. No. 7,244,256, to the present inventors and commonly assigned herewith, shows a preferred method of assembling an electrode to an electrosurgical probe using a ceramic insulating member; this technique can also be employed in manufacture of the improved electrode of the present invention.

It is also typical practice to construct the electrosurgical probe as a tubular member, so that a vacuum can be applied to the lumen of the probe to draw gasses, supplied fluid, ablated tissue, and other debris away from the surgical site. Typically the lumen communicates with the surgical site through an orifice in the electrode's active surface. In order that the ablated tissue and debris, which are typically entrained in a stream of saline solution provided for the purpose, are prevented from clogging the lumen of the probe, it is known to form the electrode's active surface such that the members providing the sharp edges that are preferred, as above, to ensure high current density are arranged to comprise a grate or filter. Larger particles of ablated tissue and debris are then caught on the active electrode surfaces of the filter and ablated into smaller particles, which can then be drawn past the active surfaces into the lumen.

For example, U.S. Pat. No. 7,150,746, also to the present inventors and commonly assigned herewith, shows the formation of the active surface of the electrode as a series of parallel rails, with the lumen of the probe in communication with the area under the active surface. This patent also teaches the provision of a further active edge at the lower end of the electrode for further ablating tissue particles that have passed through the filter provided by the outer electrode edges, to further reduce clogging of the opening of the lumen.

Despite these refinements, clogging of the lumen still occurs from time to time. The present invention is directed to further improvements in design of the electrode of electrosurgical probes, so as to further reduce clogging of the lumen of the probe by ablated tissue and other debris.

SUMMARY OF THE INVENTION

In one embodiment of the present invention, the outer active surface of the electrode defines a circumferential ring at the outer surface of the probe, such that an open circular orifice within the ring communicates with the lumen of the probe. The lumen is of greater cross-sectional area over its length than the area of the open orifice in the ring, such that flow of saline solution, with ablated tissue particles and other debris entrained therein, is accelerated through the orifice. The inner edge of the ring may be left relatively sharp to encourage ablation of particles. The result is that the orifice, which forms the portion of minimum cross-sectional area in the flow path for ablated tissue and other debris, is an active ablative surface; accordingly, any particle that is ablated to the point of passing through the orifice is unlikely to cause clogging downstream in the flow path.

In this embodiment, the orifice through the electrode can be formed by first drilling through the center of the electrode body with a drill of a first diameter, corresponding to the desired diameter of the open center of the ring. The electrode body is then drilled into from the inside using a conventional drill bit of larger diameter; the drilling operation is performed so that the drill bit does not completely penetrate the outer surface of the electrode, so that the conical tip of the drill bit forms a frusto-conical recess around the orifice at the outer surface of the electrode tip, and a relatively sharp edge is provided to the orifice at the outer surface of the electrode. The frusto-conical surface and the bore in the electrode thus together define a venturi, such that fluid passing through the orifice into the lumen of the probe accelerates as it passes by the edge of the orifice. The inside of the electrode could also be shaped to form a more gradually tapered venturi in the electrode body.

In a further embodiment, two or more orifices might be formed in the outer surface of the electrode, each mating with a tapered bore in the body of the electrode so as to define venturis; these orifices and the associated bore(s) might be circular or elongated in cross-section.

In each embodiment, the cross-sectional area of the orifice(s) is less than the cross-sectional area of any other portion of the flow path between the orifice(s) and the source of vacuum, so that any particle sufficiently ablated by the active surfaces provided at the orifice(s) to pass therethrough is unlikely to cause a clog downstream.

BRIEF DESCRIPTION OF THE DRAWINGS

The invention will be better understood if reference is made to the accompanying drawings, in which:

FIG. 3 is an exploded view of the components of the distal portion of the electrosurgical probe of the invention;

FIG. 4 is a cross-sectional view through the distal portion of the probe of the invention, including the electrode of the invention;

FIGS. 7-10, each similarly comprising end and cross-sectional views, show further embodiments of the electrodes of the invention.

DESCRIPTION OF THE PREFERRED EMBODIMENTS

Figure 1:
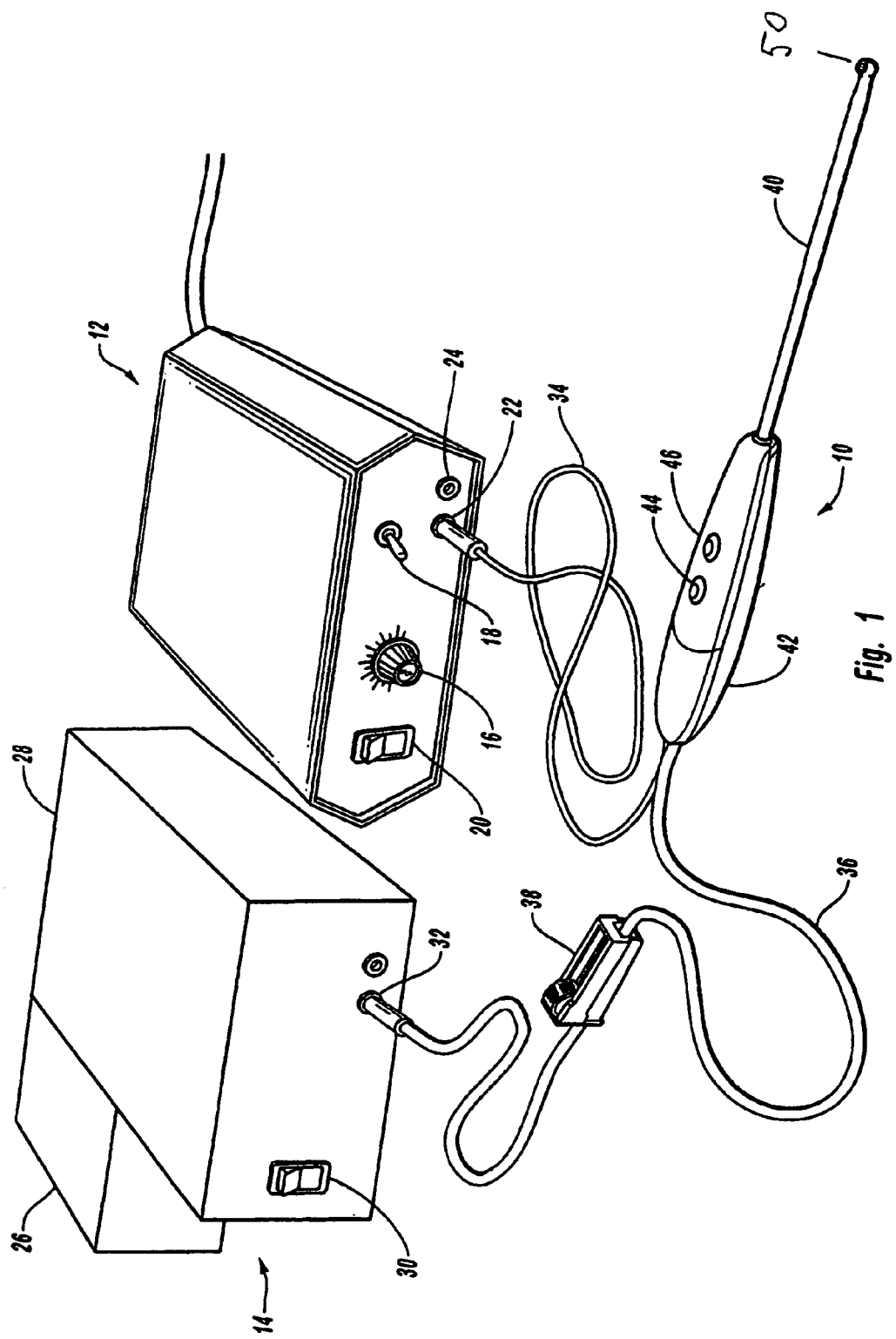
FIG. 1 shows an overall perspective view of electrosurgical apparatus according to the invention.

FIG. 1 shows an exemplary electrosurgical system comprising an electrosurgical probe assembly 10 including a gripping handle 42, an elongated probe 40, and the electrode of the invention 50, an electrosurgical generator 12, and an aspirator 14. Electrosurgical generator 12 comprises conventional circuitry for generating signals including suitable radio frequency ("RF") energy for supply to electrosurgical probe 10, in order to heat the surface of electrode 50 in order to ablate and/or coagulate tissue. Push buttons 44 and 46 on handle 42 can conveniently be used to switch the mode of operation of probe 40 between an ablation mode and a coagulation mode.

Generator 12 includes standard components, such as a potentiometer 16 for controlling the frequency and/or amplitude of the RF energy, a switch 18 for controlling the type of waveform generated, a switch 20 for turning the generator on and off, and an electrical port 22 for connecting the electrosurgical instrument 10. The RF energy is thus communicated to the electrode 50 by way of port 22, a connecting cable 34, and a conductor built into probe 10. Generator 12 also includes port 24 for connecting an electrical ground. Ground port 24 can be connected to a second electrode on the probe 10 if a bipolar probe is preferred, or can be connected to a separate grounding contact secured to the patient where a monopolar probe is preferred.

Aspirator 14 includes a pump 26, a reservoir 28, an on/off switch 30, and an aspirator port 32. Pump 26 provides negative pressure for aspirating fluids, gasses, ablated tissue and other debris through electrosurgical device 10, by way of connecting tube 36. A flow control device 38 allows a practitioner to vary the rate of aspiration through instrument 10. Aspirated fluids and debris can be collected in reservoir 28.

Those skilled in the art will recognize that many different configurations of generator 12 and aspirator 14 can be used in the present invention. For example, typical operating rooms provide a wall vacuum connection of between 200-600 mmHg, which can be employ to aspirate fluids and debris from the vicinity of the electrode 50, eliminating the necessity of a separate aspirator 14.

Figure 2:
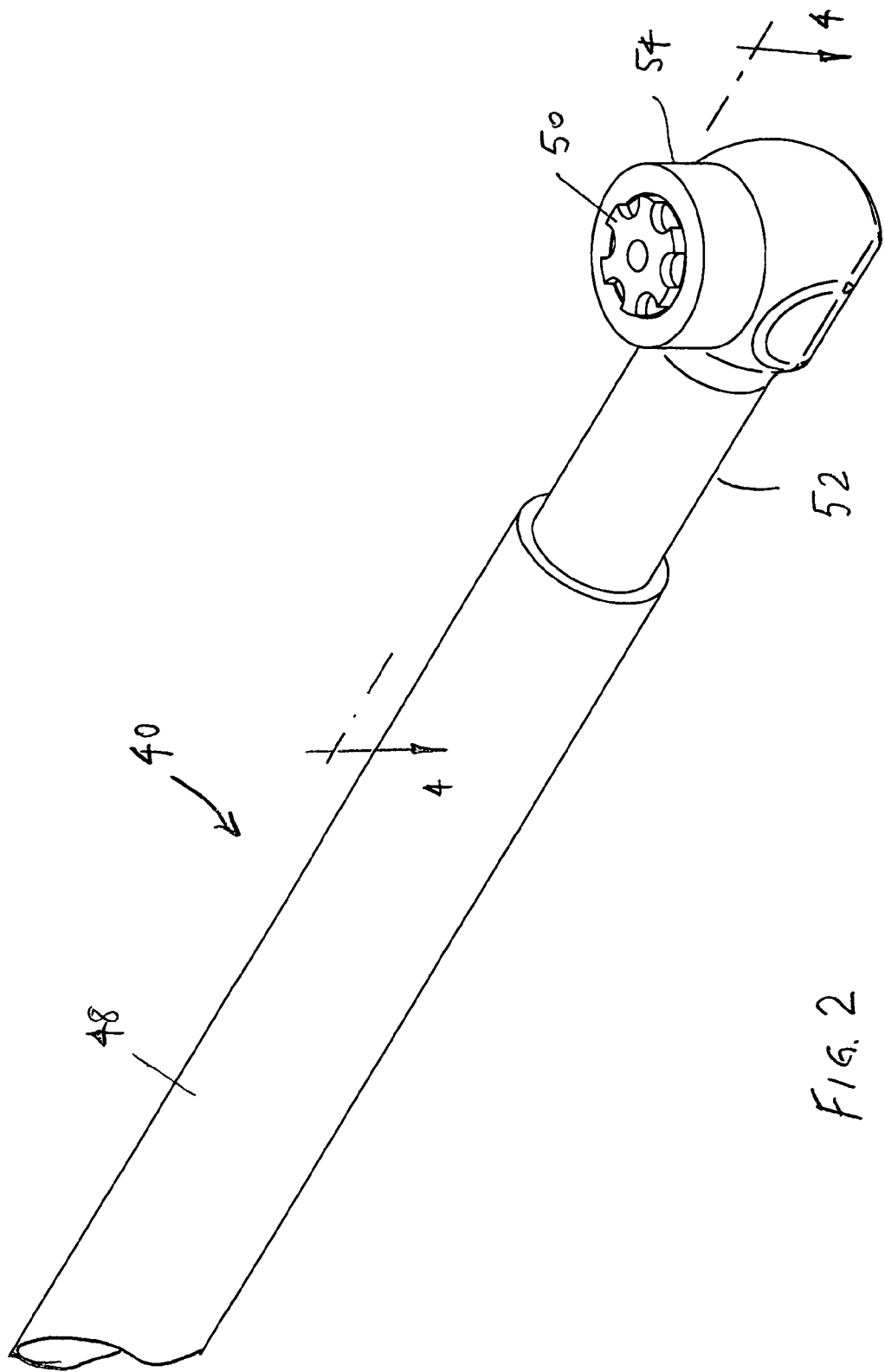
FIG. 2 shows a perspective view of the distal end of an electrosurgical probe employing the electrode of the invention.

FIGS. 2 and 3 illustrate the probe 40 of the present invention with an outer sheath 56 (shown in FIG. 5) removed to better illustrate the structure of the probe. As shown in FIG. 2, in an exemplary embodiment, probe 40 includes insulative outer tubing 48, electrode 50, a conductive electrode seat 52 carrying the RF energy from a connection (not shown) with the power cable 34 at the proximal end of the probe to the electrode 50, and an insulating bushing 54, confined between the electrode 50 and its seat 52. The electrode 50 can be threaded into the conductive electrode seat 52 or can be projection welded thereto, as discussed in detail in U.S. Pat. No. 7,244,256. Insulating bushing 54 is typically made of a highly heat resistant and electrically nonconductive material such as a ceramic, to withstand very high temperatures engendered in the arcing process.

Figure 5:
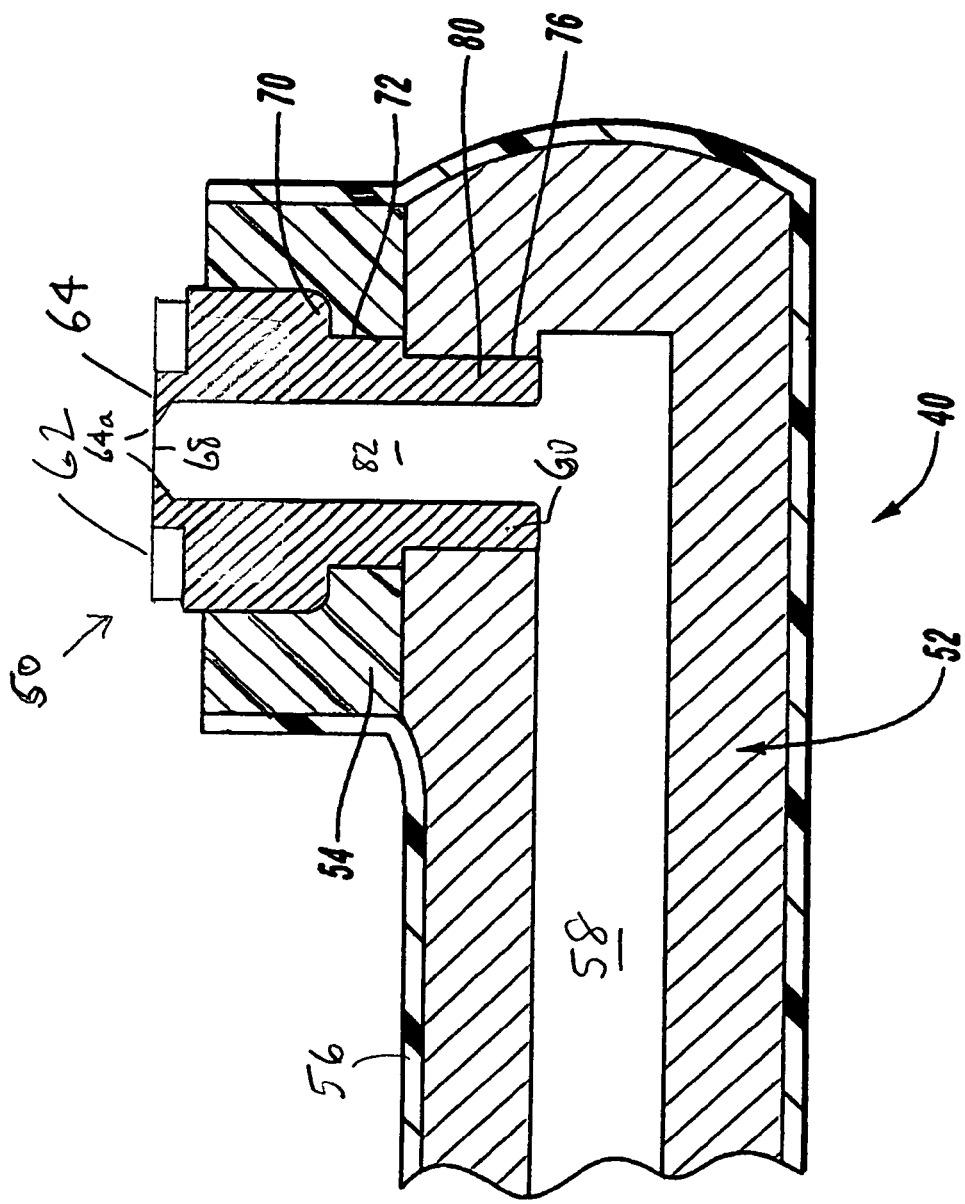
FIG. 5 is an enlarged view of a portion of FIG. 4, showing the assembly of the probe and the electrode of the invention in further detail.

As shown in further detail in FIGS. 4 and 5, electrode 50 has a proximal end 60 and a distal end 62. The active surface 64 of electrode 50 is formed on its distal end 62 and is shaped to ensure high current density in desired areas to provide reliable arcing for ablating tissue. More specifically, the edges 64a of active surface 64 create small surface areas where current discharges. The discharge of current from active surface 64 creates a plasma that can ablate tissue. Electrode 50 can also be operated so as to coagulate tissue rather ablate it. To coagulate tissue the power applied to active surface 64 is simply reduced, such that the active surface 64 does not arc. The power applied to active surface 64 creates heat that simply dissipates into surrounding tissue. This heat transfer causes coagulation rather than ablation.

In the embodiment of FIGS. 3-6, the active surface 64 of the distal end of the electrode is shaped as a generally circular ring, surrounding an orifice 68 communicating with the lumen of the probe, so that suction applied to the proximal end of the probe effectively withdraws fluid, gasses, aspirated tissue, and other debris from the surgical site. According to the invention, as discussed further below, the orifice 68 in the active surface 64 is of smaller cross-sectional area than that of the bore in the electrode and the lumen in the probe; that is, the cross-sectional area of the orifice 68 is less than the cross-sectional area of all other portions of the flow path for debris, such that any particle sufficiently ablated to pass through the orifice 68 is unlikely to become clogged downstream. Moreover, in this way the highly ablative sharp edge 64a surrounding orifice 68 forms the portion of the flow path of minimum cross-sectional area, further ensuring ablation of particles and reducing clogging. Finally, in this way, a venturi is formed by the combination of the orifice 68 and the bore 82 in the electrode 50, causing fluid flow to be accelerated past the active edges 64a of the orifice 68, and reducing or eliminating clogging.

As shown in FIGS. 4 and 5, electrode 50 and seat 52 define a lumen 58 through the center of probe 40. Lumen 58 opens near the distal end of electrode 50 for aspirating fluids, gasses, and debris from the exterior of probe 40. At the proximal end of probe 40, lumen 58 is connected to aspirator 14 (see FIG. 1), which creates negative pressure in lumen 58. The negative pressure draws gasses, fluids, and debris from the exterior of instrument 10 into lumen 58. The proximal portion of probe 40 may comprise section of tubing 48. An optional liner within tubing 48 (not shown) may also be provided and can be made of any desired material, including insulating and non-insulating materials.

As shown in FIG. 5, probe 40 will usually also include an insulating sheath 56. Insulating coating 56 prevents direct electrical contact between the metal components of probe 40 and any exterior materials. Any contact between the conductive components of probe 40 and exterior materials can result in unwanted discharge. Because of the high temperatures involved in electrosurgery, insulating coating 56 is typically made from a heat resistant material. Suitable materials for making insulating coating 56 include polyimides, nylon, polytetraflouroethylene, and the like.

As further shown in FIGS. 3-5, electrode 50 is configured to engage insulating bushing 54 to secure insulating piece 54 to electrosurgical device 10. Electrode 50 includes a retaining ledge 70 that is configured to engage lip 72 of insulating bushing 54. Retaining ledge 70 and lip 72 are configured to seat tightly to minimize the gap between electrode 50 and insulating bushing 54. Insulating bushing 54 is also seated on surface 76 of electrode seat 52. Typically, the electrode 50 and insulating bushing 54 are cooperatively configured so that the active surface 64 of electrode 50 is slightly proud of the surrounding surface of insulating bushing 54.

The present invention relates more particularly to the detailed design of the electrode. As summarized above, the electrode design according to the invention is such that the cross-sectional area of the orifice(s) in the active surface of the electrode is less than the cross-sectional area of any other portion of the flow path between the orifice(s) and the source of vacuum. This has several useful consequences. First, this fact means that any particle passing through the orifice(s) is unlikely to form a clog downstream in the flow path. Second, the fact that the orifice(s) is formed in the active surface means that any particle too large to pass through the orifice(s) will typically be ablated until it is reduced sufficiently to pass therethrough. Third, any particle that clogs the orifice will likely be caught on the active surface, so that the surgeon can "wipe it off" by rubbing the electrode against a surrounding surface. Finally, the combination of one or more orifices at the distal end of the flow path in communication with a flow path of larger cross-sectional area means that a venturi is formed, providing accelerated flow of the aspirated saline solution, aspirated tissue, gasses, and debris from the vicinity of the surgical site through the orifice(s) in the active surface of the electrode, to reduce clogging. Several embodiments of the inventive electrode designs providing this feature are shown herein, and others which are within the skill of the art are within the scope of the appended claims.

Figure 6A:
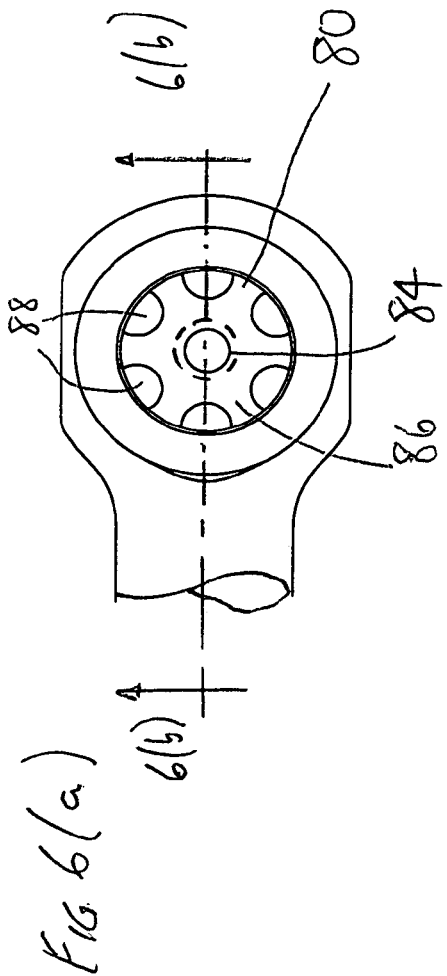
FIG. 6, comprising an end view in FIG. 6(a) and a cross-sectional view in FIG. 6(b), shows further details of a first embodiment of the electrode of the invention.
Figure 6B:
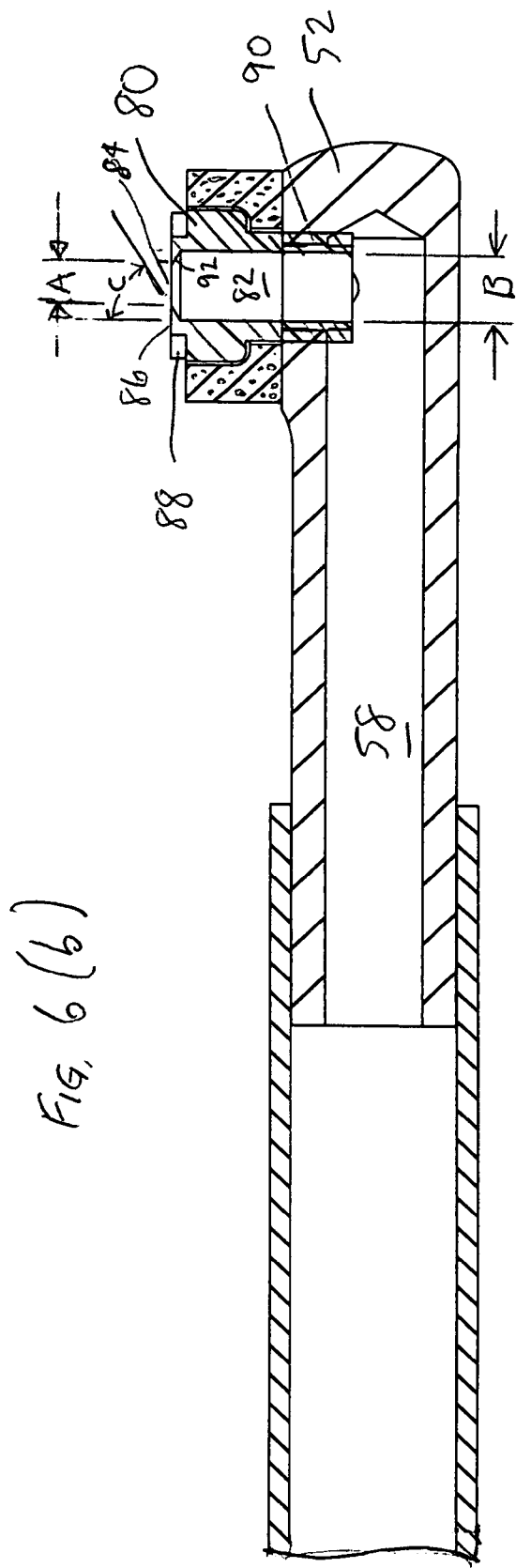

FIG. 6 shows a first embodiment of the inventive electrode, and includes an end view in FIG. 6(a) and in FIG. 6(b) a cross-section taken on the line 6(b)-6(b) of FIG. 6(a). The electrode in this embodiment is generally as in FIGS. 2-5, and FIG. 6(b) substantially corresponds to FIG. 4. As illustrated, the electrode 80 is generally cylindrical, with an internal bore 82 communicating with an orifice 84 at the outer, active surface 86 of the electrode. As illustrated, the bore 82 is of larger cross-sectional area than the orifice 84, such that a venturi comprising bore 82, a frustoconical surface 92, and orifice 84 is created within the electrode. As above, when suction is applied to the bore 82 via the lumen 58 in an associated probe, fluid velocity will be accelerated past the orifice 84, tending to reduce clogging, and any particle passing through orifice 84 is unlikely to become clogged downstream.

As also illustrated, the outer peripheral edge of the electrode may be provided with a plurality, six in the example shown, of semicylindrical recesses 88. Recesses 88 are provided to accept a spanner wrench used to apply torque to the electrode 80, so that a threaded connection indicated at 90 can be employed to secure the electrode to the seat 52. Alternatively, the electrode can be projection welded to the seat, as described in U.S. Pat. No. 7,244,256, referred to above.

The present invention also include methods for manufacturing electrode 80. Typically stainless steel will be used, but another suitably conductive metal, such as tungsten, platinum, titanium, molybdenum, nickel, or their alloys might be used. Conveniently, the venturi can be formed in the electrode by first drilling into and through a cylindrical section of the desired material from the distal end, that is, downwardly from above in the orientation of FIG. 6(b), using a drill bit of the desired dimension A of the orifice 84, typically 0.027 inches for an electrode 80 of 0.102 inches overall diameter. (As will, be appreciated, this drilling operation can be performed equally well from the inside of the electrode.) The venturi can then be completed by forming the bore 82 and the frustoconical surface 92 in a single operation. More specifically, bore 82 and frustoconical surface 92 can then be formed by drilling upwardly from below with a second, larger drill bit, typically 0.0465 inches (dimension B in FIG. 6(*b*)), while controlling the drilling operation to stop before the drill bit penetrates fully, thus leaving a frustoconical surface 92 extending between the orifice 84 and the cylindrical bore 82, thus completing the venturi.

More specifically, the depth of the drilling from below is carefully controlled such that the frustoconical surface 92 does not intersect the active outer surface 86, that is, so that the orifice 80 is not broadened out. Preferably a relatively sharp edge is formed around the edge of the orifice, improving the arc-generating properties of the electrode, but it is found to be acceptable to have a cylindrical surface from the first drilling operation remain, as long as it is not too long, no more than 0.010 inches or thereabouts. Where a conventional drill bit of 118° included tip angle is used to form bore 82 and frustoconical surface 92, the angle C formed between the frustoconical surface 92 and the axis of the bore is 59°. It is of course within the skill of the art to form the venturi using other known techniques.

Figure 7A:
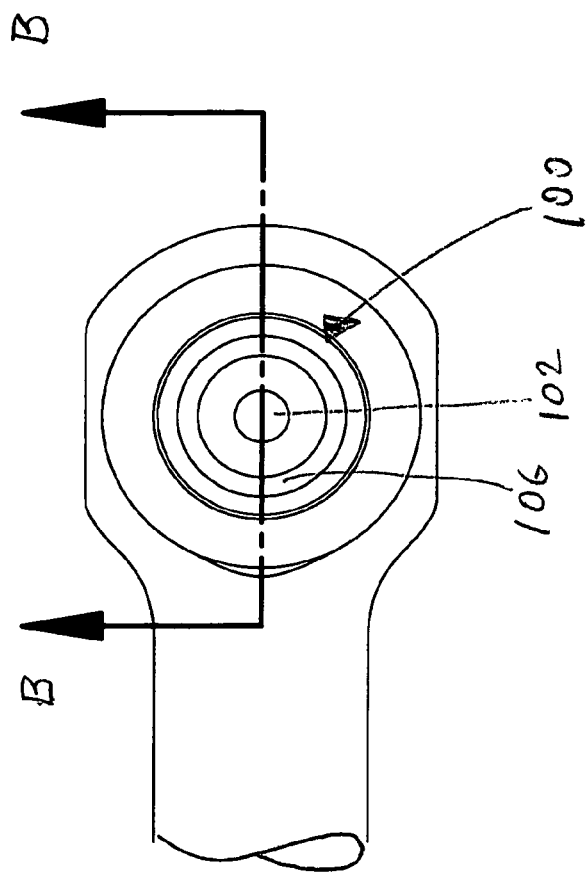
Figure 7B:
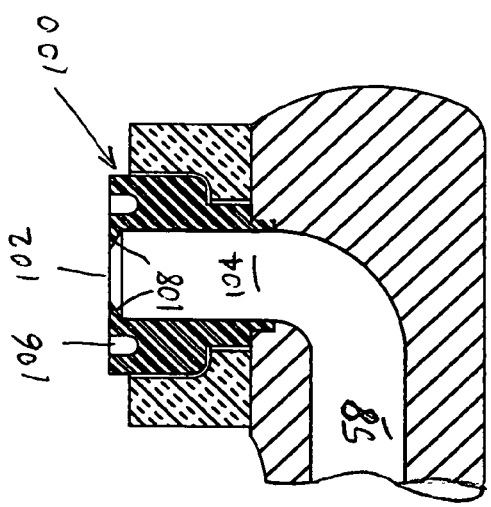

FIG. 7, comprising a similar pair of views in FIGS. 7(*a*) and (*b*), shows a second embodiment of an electrode 100 according to the invention. In this embodiment, the venturi is typically again formed by drilling into the body of the electrode from the outside of the active surface of the electrode, that is, from above in FIG. 7(*a*), with a first drill bit of the size of the desired diameter of the orifice 102. The bore 104 and frustoconical surface 108, and thus the venturi, are then formed by drilling upwardly into the electrode with a larger drill bit, of the desired diameter of the bore 104, while avoiding drilling through the active surface of the electrode, such that a frustoconical surface 108 remains.

In this embodiment, the electrode 100 is designed to be secured to the seat 52 of the probe by projection welding to the seat, as described in U.S. Pat. No. 7,244,256, referred to above. Accordingly, the body of the electrode need not be threaded, and the spanner-receiving recesses of the FIG. 6 embodiment are eliminated. Instead, in this embodiment a circular recess 106 is formed in the active surface of the electrode; the edges of this recess provide additional sharp edges at which current will be concentrated, tending to encourage the formation of an arc for ablating tissue. FIG. 7 also illustrates that it is within the scope of the invention to provide a fair transition between the bore 104 in the electrode 100 and the lumen 58 in the body of the probe, further smoothing flow by reducing turbulence.

FIGS. 8-10, each again comprising two views comparable to those of FIG. 6, show three further embodiments of the electrodes of the invention and thus illustrate further variations that might be useful in various implementations of the invention, without, however, in any way limiting its proper scope. In each of the embodiments of FIGS. 8-10, the venturi extending between the orifice(s) at the outer active surface and the lower end of the electrode, where the venturi mates with the lumen formed in the body of the probe, is made more gradual than in the FIGS. 6 and 7 embodiment. More specifically, in these additional embodiments, the cross-sectional area of the flow passageway in the electrode increases smoothly from the orifice to the entry to the lumen in the probe. Such a gradual increase in the area of the passage might prove to increase the effectiveness of the venturi, that is, increase the acceleration of fluid flow therethrough, by reduction of turbulence therein.

Thus, the electrode 110 of FIG. 8 shows a venturi 116 tapering gradually from a circular orifice 114 to mate at an exit aperture 118 with the lumen 120 formed in the body of the probe. In this embodiment, semicylindrical recesses 122 are again formed around the periphery of the active surface 124 to assist in assembly.

In the embodiment of FIG. 9, two parallel slit-like orifices 126 are formed in the active surface 132 of the electrode 134. These communicate with the lumen of the probe 138 by way of a smoothly-tapering venturi 140. Ideally, to reduce turbulence, the cross-sectional area of the orifices 126 would transition smoothly to the cross-section of the tapered venturi, but for manufacturing convenience some slight discontinuities may be required, as illustrated; these would preferably be limited as much as possible. Four recesses 136 are formed in the active surface 132 for assembly purposes.

Figures 10A, 10B:
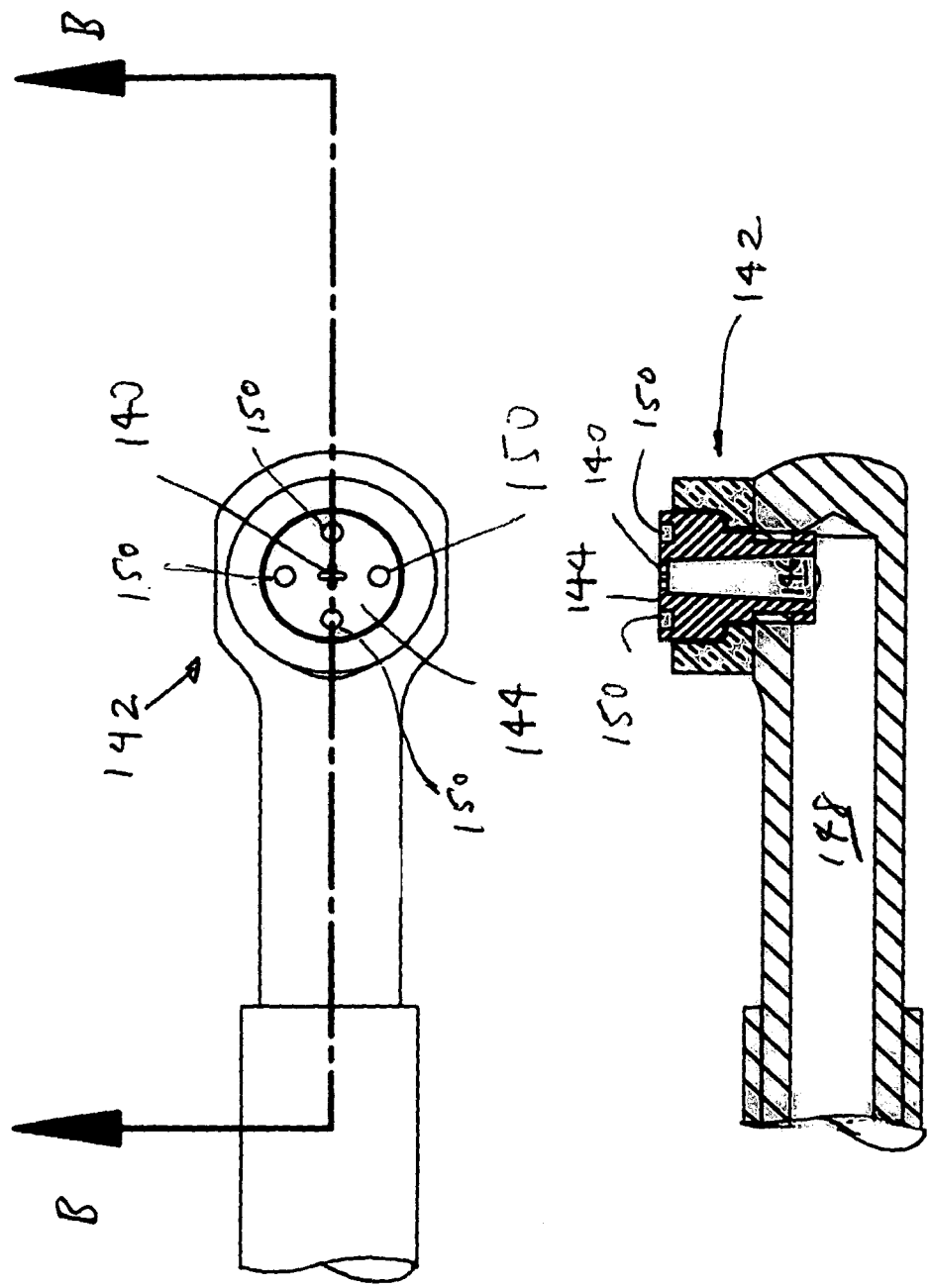

Finally, in the embodiment of FIG. 10, the orifice 140 in the active surface 144 of the electrode 142 is of generally cruciform configuration, providing considerable edge length at which current can be concentrated, leading to formation of a stable plasma. The cruciform orifice again leads into a smoothly tapering venturi 146 which mates with a lumen 148 in the probe. As above, any discontinuities in the transition between the cruciform orifice and the entry to the venturi 146 are to be minimized as much as possible, so that the cross-sectional area of the flow passageway formed thereby increases as smoothly as possible. Again, four recesses 150 are formed in the active surface 144 for assembly purposes. Alternatively, the outer periphery of the electrode could be formed to define, e.g., a hex shape, to receive a wrench for assembly purposes.

It will thus be appreciated by those of skill in the art that the fundamental principle of the invention is to provide an electrode for electrosurgery wherein one or more orifices of given cross-sectional area in the active surface of the electrode communicate with a venturi of greater cross-sectional area in the body of the electrode, and thence with a lumen in the body of the probe, so that particles passing through the orifice(s) are unlikely to become clogged downsteam, so that any particles captured at the minimum cross-sectional area of the orifice(s) are ablated there, and so that the rate of fluid flow into the orifices responsive to vacuum applied to the lumen is accelerated, tending to reduce clogging of the orifice(s) by ablated tissue and other debris at the surgical site.

Accordingly, the invention is not to be limited by the above exemplary disclosure, and may be embodied in other specific forms without departing from its spirit or essential characteristics. The described embodiments are to be considered in all respects only as illustrative and not restrictive. The scope of the invention is, therefore, indicated by the appended claims rather than by the foregoing description. All alternatives and improvements which come within the meaning and range of equivalency of the claims are to be embraced within their scope.

What is claimed is:

1. An electrosurgical instrument for ablating tissue in a surgical procedure, comprising:
   a controllable source of electrical energy;
   an elongate electrically conductive probe having a proximal end portion and a distal end portion and defining a lumen therethrough, a proximal end of said lumen being adapted to be connected to a source of vacuum; and
   an electrode disposed at the distal end portion of the probe and electrically coupled to said source of electrical energy, the electrode comprising a body having a distal end comprising an outer active surface and a proximal end, the electrode comprising:

a bore formed in the body of the electrode, said bore disposed in fluid communication with the lumen of the probe, and extending from the proximal end of the electrode toward the distal end;

said outer active surface formed on the distal end of the electrode being configured so as to define a single circular orifice in fluid communication with the bore of the electrode and being configured for aspirating gasses, fluids, ablated tissue, and other debris from a surgical site juxtaposed to the orifice, responsive to a vacuum applied to the proximal end of the lumen in the probe;

wherein an inner frustoconical surface is provided on the inside of the distal end of the body of the electrode, between the bore in the electrode and the orifice in the active surface thereof, said inner frustoconical surface being juxtaposed to the outer active surface of the electrode such that the axial length of a bore extending between said outer active surface and said inner frustoconical surface is minimized ; and wherein the total cross-sectional area of the orifice in the active surface of the electrode is less than that of the bore of the electrode, forming a venturi, whereby the rate of flow of said gasses, fluids, ablated tissue, and other debris is accelerated in the vicinity of the one or more orifices in the outer surface of the electrode.

2. The electrosurgical instrument of claim 1, wherein said circular orifice in the outer active surface of said electrode and said bore extending between said outer active surface and said inner frustoconical surface are formed by drilling into the active surface of the electrode using a first drill bit of a first diameter.

3. The electrosurgical instrument of claim 2, wherein the frustoconical surface on the inside of the distal end of the body of the electrode and the bore in the electrode are formed by a second step of drilling from a proximal end of the electrode toward the outer surface thereof with a second drill bit of second diameter larger than said first diameter of said first drill bit, said second drill bit having a conical tip, said second drilling step being controlled such that said second drill bit does not fully penetrate the outer active surface of the electrode, whereby the conical tip of the second drill bit forms said frustoconical surface on the inside of the distal end of the body of the electrode.

4. The electrosurgical instrument of claim 1, wherein the axial length of said bore extending between said outer active surface and said inner frustoconical surface is no more than about 0.010 inches.

\* \* \* \* \*